United States Patent [19]

Vogt et al.

[11] Patent Number: 4,497,747

[45] Date of Patent: Feb. 5, 1985

[54] PROCESS FOR MAKING ACETIC ANHYDRIDE

[75] Inventors: Wilhelm Vogt, Hürth; Hermann Glaser, Erftstadt; Erhard Jägers, Bornheim, all of Fed. Rep. of Germany

[73] Assignee: Hoechst Aktiengesellschaft, Frankfurt am Main, Fed. Rep. of Germany

[21] Appl. No.: 515,283

[22] Filed: Jul. 19, 1983

[30] Foreign Application Priority Data

Aug. 21, 1982 [DE] Fed. Rep. of Germany ....... 3231154

[51] Int. Cl.³ ...................... C07C 51/54; C07C 51/56
[52] U.S. Cl. ..................................... 260/546; 260/549
[58] Field of Search ................................ 260/549, 546

[56] References Cited

U.S. PATENT DOCUMENTS

| | | | |
|---|---|---|---|
| 2,729,651 | 1/1956 | Reppe et al. | 562/519 |
| 4,140,865 | 2/1979 | Fernholz et al. | 560/206 |
| 4,333,884 | 6/1982 | Kubbeler et al. | 260/549 |

Primary Examiner—Natalie Trousof
Assistant Examiner—L. Hendriksen
Attorney, Agent, or Firm—Connolly and Hutz

[57] ABSTRACT

The disclosure relates to a process for making acetic anhydride by reacting methyl acetate and/or dimethylether with carbon monoxide, if desired in admixture with up to 20 volume % hydrogen, under practically anhydrous conditions at temperatures of 120° to 270° C., under pressures of 1 to 500 bars in the presence of a catalyst system containing nickel or a nickel compound, an organic iodine or bromine compound as well as a tertiary or quaternary organic phosphorus compound. More particularly, a catalyst system containing a titanium or zirconium compound as an additional constituent is used.

4 Claims, No Drawings

PROCESS FOR MAKING ACETIC ANHYDRIDE

The present invention relates to a process for making acetic anhydride by reacting methyl acetate and/or dimethylether with carbon monoxide, which may be used in admixture with up to 20 volume % hydrogen, if desired, under practically anhydrous conditions at temperatures of 120° to 270° C. and under pressures of 1 to 500 bars in the presence of a catalyst system containing nickel or nickel compounds, an organic iodine or bromine compound and a tertiary or quaternary organic phosphorous compound.

Such process has already been described in U.S. Pat. No. 2,729,651, wherein the feed materials are basically selected from nickel complexes which comprise e.g. triphenyl-ethyl-phosphonium nickel tetriodide, while tetramethylammonium iodide and nickel iodide or nickel powder, iodine, triethylamine and ethyl iodide, for example, can also be used. Although the reaction is carried out under pressures of up to 700 bars, acetic anhydride is obtained in minor space/time-yields for reaction periods between 5 and 26 hours.

As a result of the corrosiveness of the reaction medium, it is necessary for the autoclave to be made of an alloy of Hastelloy B or C or tantalum which naturally means heavy investment of capital for effecting such carbonylation processes.

The present invention now provides a catalyst system containing a titanium or zirconium compound as an additional constituent, which permits the catalyst system described in U.S. Pat. No. 2,729,651 to be activated, i.e. the space/time yields to be considerably improved and the commercial attractiveness of the process to be critically improved.

The process of this invention should preferably be carried out with the use of an oxalkyl compound of titanium or zirconium, which may be selected e.g. from titanic acid esters, such as tetrabutyl titanate, tetramethyl titanate; titanylacetyl acetonate or zirconic acid esters, such as tetrabutyl zirconate, and also zirconiumacetyl acetonate.

Useful nickel compounds are, for example, nickel carbonyl, nickelacetyl acetonate, nickel halides, nickel acetate, nickel sulfate or nickel cyanide.

The organic iodine or bromine compounds should conveniently be selected from methyl iodide, ethyl iodide, methyl bromide or ethyl bromide. Preferred tertiary or quaternary organic phosphorus compounds are trialkyl or triarylphosphines or their phosphonium bromides or iodides, e.g. tributylphosphine, trioctylphosphine, trilaurylphosphine, triphenylphosphine, tributylmethylphosphonium iodide (bromide), trioctylmethylphosphonium iodide (bromide), trilaurylmethylphosphonium iodide (bromide) or triphenylmethylphosphonium iodide (bromide).

The reaction should preferably be carried out under pressures of 10 to 300 bars, and the individual reactants, i.e. methyl acetate or dimethylether/nickel(compound-)/iodine or bromine compound/phosphorus compound-/titanium or zirconium compound should preferably be used in a molar ratio of 1:(0.001–0.1):(0.01–1):(0.0-05–1):(0.0005–0.1).

By the addition e.g. of 15 g tetrabutyl titanate per liter of reaction solution at 200° C., it has been possible to increase by a factor of 10 to 15 the reaction velocity to acetic anhydride substantially in the absence of any significant formation of by-products.

Typically, nickel e.g. nickel tetracarbonyl has been found less significantly to accelerate the reaction under pressures lower than 200 bars at 200° C. in all those cases in which just one of the essential catalyst constituents, e.g. alkyl halide or phosphine or phosphonium salt or titanium or zirconium compound was omitted from the catalyst system. In accordance with this invention, it is also not possible for an alkyl or aryl amine to be substituted for phosphine without strong decrease of the space/time-yield of acetic anhydride. By the use of all catalyst constituents in the proportions specified in this invention, it is possible to obtain acetic anhydride in space/time-yields within the range 500 to 2000 g/l under a maximum pressure of ≦200 bars and at a reaction temperature of about 200° C.

By increasing the catalyst concentration and temperature to more than 200° C., it is even possible further to increase the space/time-yield. 6000 g $Ac_2O$ per liter per hour, for example, was obtained at 230° C. so that it would appear highly desirable for this process to be effected in small capacity flow reactors.

It is also possible for the present carbonylation reaction to be carried out in the presence of a solvent, such as acetic acid or an amide, such as N-methylpyrrolidone, N,N-diethylacetamide or a sulfur-containing solvent, such as sulfolane.

CO admixed with up to 20 volume % $H_2$ can be used as reaction gas whenever it is possible for the reaction to be carried out with the use of less pure carbon monoxide. It has even been found that the activity of re-used catalyst solutions is less affected by reaction gas containing 2 to 20 volume % hydrogen.

EXAMPLES 1 TO 5

(Comparative Example)

A 1 liter corrosionproof stainless steel autoclave provided with an agitator was charged with 250 g methyl acetate, 50 g methyl iodide and 60 g methyltributylphosphonium iodide. Next, 5 g nickel was added in each case, which was nickel powder in Example 1,
nickel chloride in Example 2,
nickel acetate in Example 3,
nickeltetracarbonyl in Example 4, and
nickelacetyl acetonate in Example 5.

The autoclave was thoroughly scavenged with argon to remove $O_2$, and a pressure of 100 bars CO was established. Next, the autoclave was heated to 197° C. The results indicated below were obtained with the use of the various nickel components. The quantity of acetic anhydride which was formed during 1 hour from 1 liter reaction solution, is indicated for the purpose of comparison.

| Catalyst<br>Ni-compound | Quantity $(CH_3CO)_2O$ formed<br>in g per 1 per hour (space/time-yield) |
|---|---|
| Ni-powder | 100 |
| $NiCl_2$ | 80 |
| $Ni(OOCCH_3)_2 \cdot 4H_2O$ | 143 |
| $Ni(CO)_4$ | 126 |
| $Ni(C_5H_7O_2)_2$ | 106 |

The introduction under pressure of 90 bars CO and 10 bars $H_2$ permitted the space/time-yields to be considerably improved under identical conditions and with use of identical feed quantities.

| Catalyst Ni-compound | Quantity $(CH_3CO)_2O$ formed in g per 1 per hour (space/time-yield) |
| --- | --- |
| Ni-powder | 221 |
| $NiCl_2$ | 150 |
| $Ni(OOCCH_3)_2 \cdot 4H_2O$ | 270 |
| $Ni(CO)_4$ | 400 |
| $Ni(C_5H_7O_2)_2$ | 320 |

By-products such as ethylidene diacetate were detectable in traces only.

EXAMPLE 6

The autoclave was fed with 250 g (3.38 mols) methyl acetate, 50 g (0.352 mol) methyl iodide, 60 g (0.174 mol) $[CH_3(C_4H_9)_3P]I$, 5 g (0.03 mol) $Ni(CO)_4$, 5 g (0.015 mol) $Ti(OC_4H_9)_4$. The reaction solution had a volume of 351 milliliters. The autoclave was scavenged, a CO pressure of 100 bars was established and the whole was heated to 197° C. The pressure in the autoclave was found to have dropped within 16 minutes from 165 to 75 bars and the temperature to have been increased by 10° C. by the reaction heat. The deep red solution was worked up by distillation and 160 g acetic anhydride, corresponding to a yield of 1710 g acetic anhydride per liter reaction solution per hour, was obtained.

EXAMPLE 7

The quantities of feed materials and reaction time were as in Example 6 but 5 g (0.03 mol) tetramethyl titanate was substituted for the 5 g tetrabutyl titanate. The acetic anhydride obtained was worked up distillatively and then subjected to gas-chromatographic analysis. 165 g corresponding to a yield of 1753 g $(CH_3CO)_2O$ per liter reaction solution per hour was obtained.

EXAMPLE 8

The quantities of feed material were as in Example 6 but 5 g (0.01 mol) zirconiumacetyl acetonate was substituted for tetrabutyl titanate. 161 g acetic anhydride corresponding to 1450 g $(CH_3CO)_2O$ per liter reaction solution per hour, was obtained within 19 minutes under identical reaction and work-up conditions.

EXAMPLE 9

The conditions were as in Example 6 but 5 g (0.02 mol) nickel acetyl acetonate was substituted for nickel carbonyl. 161 g acetic anhydride corresponding to 1450 g $(CH_3CO)_2O$ per liter reaction solution per hour, was obtained within 19 minutes.

EXAMPLE 10

250 g methyl acetate, 50 g methyl iodide, 7.7 g (0.03 mol) nickelacetonyl acetonate, 11.5 g (0.03 mol) butyl zirconate, and 60 g methyltributylphosphonium iodide were used. 90 bars CO and 10 bars $H_2$ were introduced. 159 g acetic anhydride corresponding to 1600 g acetic anhydride per liter reaction solution per hour, was obtained at 197° C. within 17 minutes.

As a result of the high reaction velocity, it was not possible exactly to maintain the reaction temperature which indeed exceeded the nominal value by up to 10° C.

EXAMPLE 11

The procedure was as in Example 10 but a pressure of 100 bars CO without hydrogen was established. 161 g acetic anhydride corresponding to 1530 g per liter reaction volume per hour was obtained within 18 minutes.

EXAMPLE 12

The first runnings consisting of methyl iodide and unreacted methyl acetate which were obtained during the distillative work up described in Example 6 were admixed with fresh methyl acetate and the mixture was used again together with distillation residue. After altogether 5 recycle operations, the efficiency could not be found to have been reduced. The CO-gas introduced under pressure contained 10 volume % hydrogen. The average yields were 1600 g $(CH_3CO)_2O$ per liter reaction solution per hour.

EXAMPLE 13

The 1 liter autoclave was charged with 120 g (0.84 mol) $CH_3I$, 25 g (0.146 mol) $Ni(CO)_4$, 150 g (0.435 mol) $CH_3(C_4H_9)_3PI$, and 5 g (0.03 mol) $Ti(OCH_3)_4$. Next, 100 g (2.17 mols) dimethylether was introduced and a CO pressure of 90 bars was established. The whole was heated to 185° C. and a maximum pressure of 155 bars was found to establish. The reaction pressure dropped to 90 bars within 10 minutes. CO was introduced again, three times. The total CO absorption corresponded to a pressure decrease of 160 bars and took 1 hour. After work up, 156 g acetic anhydride and 16 g methyl acetate were obtained.

We claim:

1. A process for making acetic anhydride by reacting methyl acetate or dimethylether with carbon monoxide unter practically anhydrous conditions at temperatures of 120° to 270° C., under pressures of 1 to 500 bars in the presence of a catalyst system containing nickel or a nickel compound, an organic iodine or bromine compound as well as a tertiary or quaternary organic phosphorus compound, which comprises using a catalyst system containing a titanium or zirconium compound as an additional constituent.

2. A process as claimed in claim 1, wherein the catalyst contains an oxyalkyl compound of titanium or zirconium.

3. A process as claimed in claim 1, wherein the methyl acetate or dimethylether/nickel(compound)/iodine or bromine compound/phosphorus compound/titanium or zirconium compound are used in a molar ratio of 1:(0.001–0.1):(0.01–1):(0.005–1):(0.0005–0.1).

4. A process as claimed in claim 1, wherein carbon monoxide is used in admixture with up to 20 volume % hydrogen.

* * * * *